United States Patent

Bouchet et al.

[11] Patent Number: 6,107,488
[45] Date of Patent: Aug. 22, 2000

[54] PHENYLIMIDAZOLIDINE PREPARATION PROCESS

[75] Inventors: Raphael Bouchet, Pantin; Michel Delthil, Noisy-le-Sec; Daniel Guilmard, Roissy-en-Brie; Philippe Mackiewicz, Livry-Gargan, all of France

[73] Assignee: Hoechst Marion Roussel, France

[21] Appl. No.: 09/068,846

[22] PCT Filed: Nov. 14, 1996

[86] PCT No.: PCT/FR96/01794

§ 371 Date: May 15, 1998

§ 102(e) Date: May 15, 1998

[87] PCT Pub. No.: WO97/18197

PCT Pub. Date: May 22, 1997

[30] Foreign Application Priority Data

Nov. 16, 1995 [FR] France ................................. 95 13589

[51] Int. Cl.⁷ ........................ C07D 233/72; C07D 491/10
[52] U.S. Cl. .................... 548/301.4; 548/320.5; 548/321.1; 548/320.1
[58] Field of Search ............... 548/320.1, 320.5, 548/321.1

[56] References Cited

U.S. PATENT DOCUMENTS

| 3,798,233 | 3/1974 | Akiba et al. ................. 548/321.1 |
| 3,818,032 | 6/1974 | Moser et al. ................ 548/320.1 X |
| 3,846,441 | 11/1974 | Mine et al. ................... 548/321.1 |
| 4,407,814 | 10/1983 | Bernauer et al. ................ 424/273 R |
| 4,427,438 | 1/1984 | Nagano et al. .............. 548/321.1 X |
| 5,166,358 | 11/1992 | Seuron et al. ................. 548/321.1 |
| 5,411,981 | 5/1995 | Gaillard-Kelly et al. ............. 514/386 |
| 5,589,497 | 12/1996 | Claussner et al. ................. 514/386 |

FOREIGN PATENT DOCUMENTS 0436426  7/1991  European Pat. Off. .

OTHER PUBLICATIONS

Camus et al, J. Pharmacol. Exp. Ther., vol. 259 (3) pp. 1247 to 1255, 1991.
P. Camus et al, "Pharmacokinetics . . . Rat Lung", Chemical Abstracts, vol. 116, No. 19, May 11, 1992, Abstract No. 187418w.

S. Hitoshi et al, "Preparation . . . Agrochemical Intermediates", Chemical Abstracts, vol. 109, No. 15, Oct. 10, 1988, Abstract No. 128548w.

J.F. Salellas et al, "Nuclear Halogenation . . . Derivatives", Chemical Abstracts, vol. 45, No. 7, Apr. 10, 1951.

Primary Examiner—Floyd D. Higel
Attorney, Agent, or Firm—Bierman, Muserlian and Lucas

[57] ABSTRACT

A subject of the invention is a preparation process for the products of formula (I):

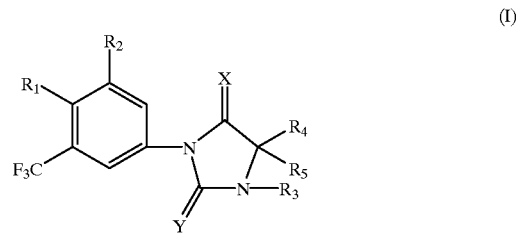

in which $R_1$ and $R_2$ represent in particular hydrogen, cyano, halogen or amino, $R_3$ represents in particular hydrogen or hydroxyl alkyl, $R_4$ and $R_5$ represent in particular optionally substituted alkyl, X and y represent oxygen or sulphur, characterized in that a product of formula (A):

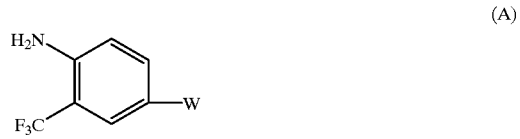

is prepared in which W represents a halogen atom or a hydantoin derivative, which is subjected to various reactions in order to obtain the products of formula (I), all their isomers and their salts.

9 Claims, No Drawings

PHENYLIMIDAZOLIDINE PREPARATION PROCESS

This application is a 371 of PCT/FR96/01794 filed Nov. 14, 1996.

The present invention relates to a new preparation process for phenyl imidazolidine derivatives.

Therefore a subject of the present invention is a new preparation process for the products of formula (I):

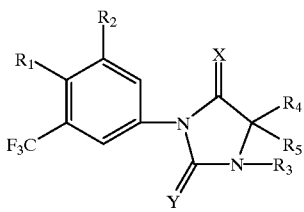

(I)

in which:

R₁ and R₂, identical or different, are chosen from the hydrogen atom, halogen atoms and the following radicals: alkyl, alkenyl, alkynyl, alkyloxy, alkenyloxy, alkynyloxy, phenyl, phenoxy, nitro, crifluoro-methyl, acyl, cyano, amino, monoalkylamino, dialkylamino, free, esterified, amidified or salified carboxy, R₃ is chosen from the hydrogen atom and alkyl, alkenyl, alkynyl, aryl and arylalkyl radicals, all these radicals being optionally substituted by one or more substituents chosen from halogen atoms, the following radicals: optionally esterified, etherified or protected hydroxyl, alkoxy, alkenyloxy, alkynyloxy, trifluoromethyl, mercapto, cyano, acyl, acyloxy, free, esterified, amidified or salified carboxy, amino, mono- and dialkylamino, arylthio and cyclic radicals containing 3 to 6 members, the alkyl, alkenyl or alkynyl radicals being more optionally interrupted by one or more oxygen, nitrogen or sulphur atoms, all the sulphur atoms being optionally oxidized in the form of the sulphoxide or sulphone, the aryl and aralkyl radicals being moreover optionally substituted by an alkyl, alkenyl or alkynyl radical, R₄ and R₅:

either are identical or different and represent a hydrogen atom or an alkyl radical, optionally substituted by one or more substituents chosen from halogen atoms, the optionally esterified, etherified or protected hydroxyl radical and phenylthio and alkylthio radicals, in which the sulphur atom can be oxidized into the sulphoxide or sulphone and being optionally substituted by one or more radicals chosen from halogen atoms and optionally esterified, etherified or protected hydroxyl radicals, free, esterified, amidified or salified carboxy radicals, amino, mono- and dialkylamino radicals, or form together a heterocyclic radical with 4 to 6 members containing an oxygen or sulphur atom, X and Y, identical or different, represent an oxygen or sulphur atom, said products of formula (I) being in all possible racemic, enantiomeric or diastereoisomeric isomer forms, as well as the addition salts with mineral and organic acids or mineral and organic bases of said products of formula (I), characterized in that:

a) a product of formula (A):

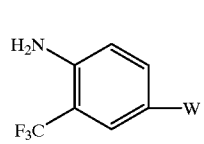

(A)

is prepared, in which w represents a halogen atom or a hydantoin derivative of formula:

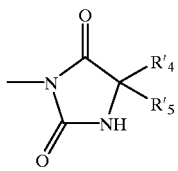

in which R'₄ and R'₅ have the meanings indicated above for R₄ and R₅ in which the optional reactive functions are optionally protected, by reacting on the compound of formula (II):

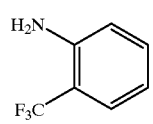

(II)

either first of all, a compound of formula (III):

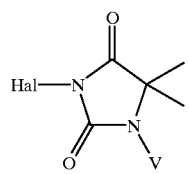

(III)

in which Hal represents a halogen atom and V represents a hydrogen atom or a halogen atom, then the compound of formula (B):

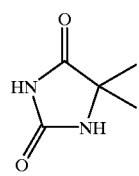

(B)

in order to obtain the product of formula (A₁):

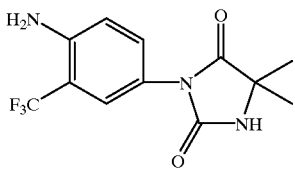

corresponding to the product of formula (A) in which W represents the dimethylhydantoin radical:

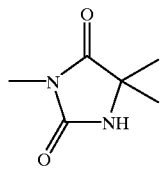

or N-bromosuccinimide in dimethylformamide, or the compound of formula (III) as defined above, in order to obtain the product of formula (A₂):

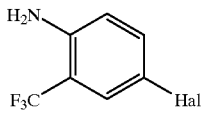

in which Hal represents a bromine atom or another halogen tom, which can be reacted with a compound of formula (IV):

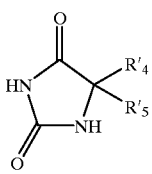

in which R'₄ and R'₅ have the meanings indicated above, in order to obtain the product of formula (A₃):

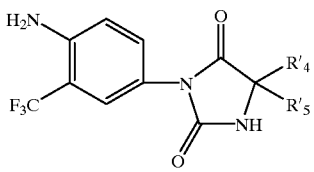

corresponding to the product of formula (A) in which W represents the radical:

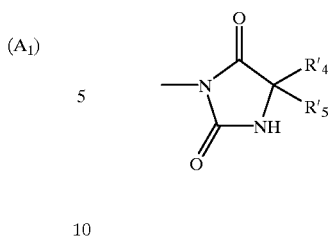

in which R'₄ and R'₅ have the meanings indicated above, b) if necessary and if desired, the product of formula (A) thus obtained is subjected to one or more of the following reactions, in any order:

i) a diazotation reaction in order to obtain the product of formula (V):

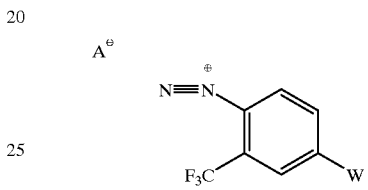

in which A⁻ represent an anion of a halogen atom or of a halogenated derivative and W has the meaning indicated above, which can be subjected to a halogenation reaction in order to obtain the product of formula (F₁):

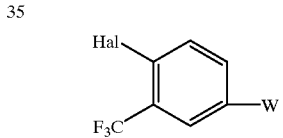

in which Hal and W have the meanings indicated above, which can be subjected to a substitution reaction on the halogen atom by a metallic derivative of formula (VI):

R'₁—M    (VI)

in which M represents a metal and R'₁ has the meaning indicated above for R₁, in which the optional reactive functions are optionally protected, in order to obtain the product of formula (F₂):

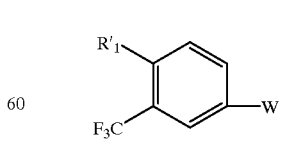

in which R'₁ and W have the meanings indicated above, ii) a halogenation reaction in order to obtain the product of formula (F₃):

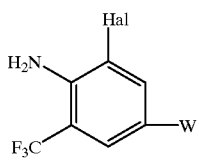

(F₃)

in which Hal represents a halogen atom and W has the meaning indicated above, which can:
either be subjected to a substitution reaction on the halogen atom, by a metallic derivative of formula (VII):

$$R'_2\text{-M} \quad (VII)$$

in which M represents a metal and $R'_2$ has the meaning indicated above for $R_2$ in which the optional reactive functions are optionally protected, in order to obtain the product of formula ($F_4$):

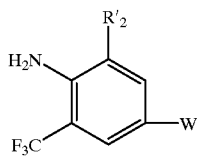

(F₄)

in which $R'_2$ and W have the meanings indicated above, which can be subjected to the successive reactions, defined above in i), of diazotation of the amino radical, then halogenation and finally substitution by the compound of formula (VI) in order to obtain the product of formula ($F_5$):

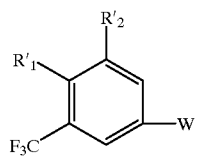

(F₅)

in which $R'_1$, $R'_2$ and W have the meanings indicated above, or is subjected to a diazotation-halogenation reaction in order to obtain the product of formula ($F_6$):

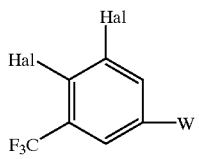

(F₆)

in which the two halogen atoms represented by Hal are identical or different and W has the meaning indicated above, which can be subjected to a substitution reaction on the halogen atoms by the compound of formula (VI) or (VII) as defined above, in order to obtain the product of formula ($F_5$) as defined above in which $R'^1$ and $R'_2$ are identical, which products of formulae ($F_1$), ($F_2$), ($F_3$), ($F_4$), ($F_5$) and ($F_6$) when W represents a halogen atom, can, if necessary and if desired, be reacted with the product of formula (IV), as defined above, in order to obtain the product of formula (I'):

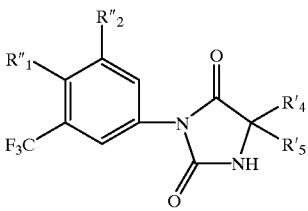

(I')

in which $R''_1$ and $R''_2$ are such that:
either $R''_2$ represents a hydrogen atom and $R''_1$ represents a halogen atom or $R'_1$ as defined above,
or $R''_2$ represents a halogen atom and $R''_1$ represents an amino radical or a halogen atom,
or $R''_2$ represents $R'_2$ as defined above and $R''_1$ represents an amino radical or $R'_1$ as defined above,
which products of formulae ($A_1$), ($A_3$) and (I'), if appropriate and if necessary, or if desired, are subjected to any one or more of the following reactions, in any order:
 a) an elimination reaction of the optional protective groups which can be carried by $R''_1$, $R''_2$, $R'_4$ and $R'_5$,
 b) a conversion reaction of the >C=O into the >C=S group,
 c) the action of a reagent of formula Hal-$R'_3$ in which $R'_3$ has the values of $R_3$ as defined in claim 1, with the exception of the hydrogen value and in which the optional reactive functions are optionally protected and Hal represents a halogen atom, in order to obtain products of formula (I) as defined in claim 1, then, if desired, the action on these products of an agent for eliminating the optional protective groups which can be carried by $R'_3$ or if appropriate, the action of an esterification, amidification or salification agent,
 d) a conversion reaction of the amino radical into a nitro radical.

For the definition of the substituents indicated above and in what follows, the definitions used can have the following values:

By halogen, is meant of course, fluorine, chlorine, bromine or iodine atoms.

The term alkyl designates a linear or branched alkyl radical having at most 12 carbon atoms, such as for example the following radicals: mechyl, ethyl, propyl, isopropyl, butyl, isobutyl, sec-butyl, tert-butyl, pentyl, isopentyl, sec-pentyl, tert-pentyl, neo-pentyl, hexyl, isohexyl, sec-hexyl, tert-hexyl, heptyl, octyl, decyl, undecyl, dodecyl.

The alkyl radicals having at most 6 carbon atoms are preferred and in particular the methyl, ethyl, propyl, isopropyl, pentyl or hexyl radicals.

The term alkenyl designates a linear or branched alkenyl radical having at most 12 carbon atoms such as for example the vinyl, allyl, 1-propenyl, butenyl, pentenyl, hexenyl radicals.

Among the alkenyl radicals, those with 6 carbon atoms are preferred such as the allyl, propenyl, butenyl, pentenyl or hexenyl radicals.

The term alkynyl designates a linear or branched alkynyl radical having at most 12 carbon atoms, such as for example the ethynyl, propargyl, butynyl, pentynyl or hexynyl radicals.

Among the alkynyl radicals, those with 4 carbon atoms are preferred such as the propargyl radical.

The term alkoxy designates a linear or branched radical containing at most 12 carbon atoms and preferably 6 such as preferably methoxy, ethoxy, propoxy or isopropoxy radicals, but also linear, secondary or tertiary butoxy, pentyloxy or hexyloxy.

the term alkenyloxy radical designates a linear or branched radical containing at most 12 carbon atoms and preferably 6, such as for example an allyloxy, 1-butenyloxy or pentenyloxy radical, the term alkynyloxy radical designates a linear or branched radical containing at most 12 carbon atoms and preferably at most 5, such as for example a propargyloxy, butynyloxy or pentynyloxy radical.

By acyl radical is preferably meant a radical having at most 7 carbon atoms such as the formyl, acetyl, propionyl, butyryl or benzoyl radical, but also the valeryl, hexanoyl, acryloyl, crotonoyl or carbamoyl radical.

By monoalkylamino radical is preferably meant the radicals in which the alkyl contains at most 4 carbon atoms. The methylamino, ethylamino, propylamino or butyl (linear or branched) amino radicals can be mentioned.

Similarly, by dialkylamino radical is preferably meant the radicals in which the alkyl contains at most 4 carbon atoms. For example the dimethylamino, diethylamino, methylethylamino radicals can be mentioned.

The carboxy radical or radicals of the products of formula (I) can be salified, amidified or esterified by the various groups known to a man skilled in the art.

By esterified carboxy is meant for example the alkyloxycarbonyl radicals such as for example methoxycarbonyl, ethoxycarbonyl, propoxycarbonyl, n-butyl, tert-butyloxycarbonyl, or also benzyloxycarbonyl radicals, these alkyl radicals being able to be substituted by one or more radicals chosen for example from halogen atoms, hydroxyl, alkoxy, acyl, alcyloxy, alkylthio, amino or aryl radicals such as, for example, in the chloromethyl, hydroxypropyl, propionyloxymethyl, methylthiomethyl, dimethylaminoethyl, benzyl or phenethyl groups.

There can be mentioned the radicals formed with the remainders of easily cleavable esters such as methoxymethyl, ethoxymethyl radicals; acyloxyalkyl radicals such as pivaloyloxymethyl, pivaloyloxyethyl, acetoxymethyl or acetoxyethyl; alkyloxycarbonyloxy alkyl radicals such as the methoxycarbonyloxy methyl or ethyl radicals, isopropyloxycarbonyloxy methyl or ethyl radicals.

A list of such ester radicals can be found for example in the European Patent EP 0,034,536.

By amidified carboxy is meant the groups of —CON($R_6$) ($R_7$) type in which the identical or different $R_6$ and $R_7$ radicals represent a hydrogen atom or an alkyl radical having 1 to 4 carbon atoms such as the methyl, ethyl, propyl, isopropyl, butyl, isobutyl, sec-butyl or tert-butyl radicals.

In the groups defined above, —N($R_6$) ($R_7$) therefore represents the amino radical, or a monoalkylamino or diethylamino radical as defined above, but can also represent a heterocycle formed by $R_6$ and $R_7$ with the nitrogen atom to which they are attached which may or may not contain an additional heteroatom. The pyrrolyl, imidazolyl, indolyl, piperidino, morpholino, piperazinyl radicals can be mentioned. There are preferred the piperidino, morpholino radicals or piperazinyl radicals optionally substituted on the second nitrogen atom, such as for example in methylpiperazinyl, fluoro-methylpiperazinyl, ethylpiperazinyl, propylpiperazinyl, phenylpiperazinyl or benzylpiperazinyl: in these last two radicals, the phenyl and benzyl radicals can be substituted, such as for example in chlorophenyl or trifluorophenyl.

By salified carboxy is meant the salts formed for example with equivalent of sodium, potassium, lithium, calcium, magnesium or ammonium. The salts formed with organic bases such as methylamine, propylamine, trimethylamine, diethylamine, triethylamine, N,N-dimethylethanolamine, tris (hydroxymethyl) amino methane, ethanolamine, pyridine, picoline, dicyclohexylamine, morpholine, benzylamine, procaine, lysine, arginine, histidine, N-methylglucamine can also be mentioned.

The sodium salt is preferred.

By aryl is meant the carbocyclic aryl radicals such as phenyl or naphthyl or the monocyclic heterocyclic aryl radicals with 5 or 6 members or constituted by condensed rings, containing one or more heteroatoms preferably chosen from oxygen, sulphur and nitrogen. Among the heterocyclic aryls with 5 members the furyl, thienyl, pyrrolyl, thiazolyl, oxazolyl, imidazolyl, thiadiazolyl, pyrazolyl, isoxazolyl, tetrazolyl radicals can be mentioned.

Among the heterocyclic aryls with 6 members, the pyridyl, pyrimidinyl, pyridazinyl, pyrazinyl radicals can be mentioned.

Among the condensed aryl radicals, the indolyl, benzofuranyl, benzothienyl, quinoleinyl radicals can be mentioned.

The phenyl, tetrazolyl and pyridyl radicals are preferred.

By arylalkyl is meant the radicals resulting from the combination of the alkyl radicals and the aryl radicals mentioned above.

The benzyl, phenylethyl, pyridylmethyl, pyridylethyl or tetrazolylmethyl radicals are preferred.

By esterified, etherified or protected hydroxyl radical, is meant the

—O—C-alphal, alpha$_2$—O—alpha$_3$ or —O—P radicals respectively, $$\underset{O}{\|}$$

formed from an —OH hydroxyl radical, according to the usual methods known to a man skilled in the art and in which P represents a protective group and alpha$_1$, alpha$_2$ and alpha$_3$ represent in particular an alkyl, alkenyl, alkynyl, aryl or arylalkyl radical having at most 12 carbon atoms and optionally substituted as defined above.

Examples of protective group P, as well as the formation of the protected hydroxyl radical, are given in particular in the usual book known to a man skilled in the art: Protective Groups in Organic Synthesis, Theodora W. Greene, Harvard University, published in 1981 by Wiley-Interscience Publishers, John Wiley & Sons.

The protective group of the hydroxyl radical which can be represented by P, can be chosen for example from the following list: formyl, acetyl, chloroacetyl, bromoacetyl, dichloroacetyl, trichloroacetyl, trifluoroacetyl, methoxyacetyl, phenoxyacetyl, benzoyl, benzoylformyl, p-nitrobenzoyl. The following groups can also be mentioned: ethoxycarbonyl, methoxycarbonyl, propoxycarbonyl, βββ-trichloroethoxycarbonyl, benzyloxycarbonyl, tert-butoxycarbonyl, 1-cyclo propylethoxycarbonyl, tetrahydropyrannyl, tetrahydrothiopyranyl, methoxytetrahydropyranyl, trityl, benzyl, 4-methoxybenzyl, benzhydryl, trichloroethyl, 1-methyl 1-methoxyethyl, phthaloyl, propionyl, butyryl, isobutyryl, valeryl, isovaleryl, oxalyl, succinyl and pivaloyl, phenylacetyl, phenylpropionyl, mesyl, chlorobenzoyl, para-nitrobenzoyl, para-tert-butylbenzoyl, caprylyl, acryloyl, methylcarbamoyl, phenylcarbamoyl, naphthylcarbamoyl.

P can in particular represent the

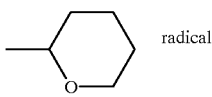 radical or also a derivative of silicon such as trimethylsilyl.

By acyloxy radical is meant the radicals in which the acyl radicals have the meaning indicated above and for example the formyloxy, acetoxy, propionyloxy, butyryloxy or benzoyloxy radicals.

the term arylthio radical preferably designates the radicals in which the aryl radical represents the radicals as defined above such as, for example, in phenylthio, pyridylthio, pyrimidylthio, imidazolylthio or N-methyl-imidazolylthio, the term alkylthio radical preferably designates the radicals in which the alkyl radical is as defined above such as, for example, in methylthio, ethylthio, propylthio, isopropylthio, butylthio, sec-butylthio, tert-butylthio, isopentylthio or isohexylthio; the alkylthio radical is optionally substituted such as, for example, in hydroxymethylthio, aminoethylthio, haloalkylthio such as preferably bromoethylthio, trifluoromethylthio, trifluoroethylthio or also pentafluoroethylthio, arylalkylthio such as, for example, benzylthio or phenechylthio.

By cyclic radical containing 3 to 6 members is meant a carbocyclic or heterocyclic radical optionally containing one or more heteroatoms chosen from sulphur, oxygen or nitrogen atoms.

By carbocyclic radical is meant in particular the cycloalkyl radical which preferably designates the cyclopropyl, cyclobutyl radicals and quite particularly the cyclopentyl, cyclohexyl and cycloheptyl radicals.

By heterocyclic radical containing one or more heteroatoms is preferably meant the saturated, heterocyclic, monocyclic radicals such as for example the following radicals: oxirannyl, oxolannyl, dioxolannyl, pyrrolidinyl, imidazolidinyl, pyrazolidinyl, piperidyl, piperazinyl or morpholinyl.

By alkyl, alkenyl or alkynyl radicals optionally interrupted by a heteroatom chosen from sulphur, oxygen or nitrogen atoms is meant the radicals containing one or more of these atoms identical or different in their structure, these heteroatoms obviously not being able to be situated at the end of the radical. There can be mentioned, for example, the alkoxyalkyl radicals such as methoxymethyl, methoxyethyl or propyloxypropyl, the alkoxyalkoxyalkyl radicals such as methoxyethoxymethyl or also the alkylthioalkyl radicals such as for example propylthiopropyl, propylthioethyl, methylthiomethyl or also N-methyl N-propylaminopropyl.

In all these radicals, the sulphur atoms can be non-oxidized as in the alkylthio, arylthio radicals or on the contrary be oxidized to produce the alkylsulphinyl, arylsulphinyl, alkylsulphonyl, or arylsulphonyl radicals: alkylsulphinyl and alkylsuiphonyl designate radicals in which the alkyl radical is chosen for example from the values indicated above for the alkyl radical such as for example methylsulphinyl, ethylsulphinyl, methylsulphonyl or ethylsulphonyl radicals, arylsulphinyl and arylsuldhonyl designate arylthio radicals, in which the aryl radical is chosen, for example, from the values indicated above for the aryl radical such as for example the following radicals: phenyl-sulphinyl or -sulphonyl, pyridyl-sulphinyl or -sulphonyl, pyrimidyl -sulphinyl or -sulphonyl, imidazolyl-sulphinyl or -sulphonyl or N-methylimidazolyl-sulphinyl or -sulphonyl.

$R_4$ and $R_5$ can in particular form together the following heterocycles:

 

 

As particular examples of alkyl radicals substituted by one or more halogens or haloalkyl, there can be mentioned the monofluoro, chloro, bromo or iodomethyl or -ethyl, difluoro, dichloro or dibromomethyl, trifluoromethyl or pentafluoroethyl radicals.

As particular examples of alkoxy radicals substituted by one or more halogens or haloalkoxy, there can be mentioned the bromoethoxy, trifluoromethoxy, trifluoroethoxy or also pentafluoroethoxy radicals.

As particular examples of substituted aryl or aralkyl radicals, there can be mentioned those in which the phenyl radical is substituted by one or more radicals chosen from iodine, chlorine or bromine atoms, methoxy, trifluoromethyl, cyano or amino radicals.

When the products of formula (I) as defined above contain an amino radical salifiable by an acid it is understood that these acid salts also form part of the invention.

The addition salts with mineral or organic acids of the products of formula (I) can be, for example, the salts formed with the following acids: hydrochloric, hydrobromic, hydroiodic, nitric, sulphuric, phosphoric, propionic, acetic, formic, benzoic, maleic, fumaric, succinic, tartaric, citric, oxalic, glyoxylic, aspartic, ascorbic, alkylmonosulphonic such as for example methanesulphonic, ethanesulphonic, propanesulphonic, alkyldisulphonics such as for example methanedisulphonic, alpha, beta-ethanedisulphonic, arylmonosulphonics such as benzenesulphonic and aryldisulphonic.

More particularly there can be mentioned the salts formed with hydrochloric or methanesulphonic acids for example.

A particular subject of the present invention is the preparation process as defined above for the products of formula (I) as defined above in which:

$R_1$ and $R_2$, identical or different, are chosen from the hydrogen atom, halogen atoms and alkyl, alkenyl, alkynyl, cyano, trifluoromethyl, amino, monoalkylamino and dialkylamino radicals, $R_3$ represents a hydrogen atom, an alkyl radical, optionally interrupted by one or more oxygen or sulphur atoms, a phenyl or pyridyl radical, these radicals being optionally substituted by one or more radicals chosen from halogen atoms, the following radicals: phenyl, optionally esterified, etherified or protected ahydroxyl, alkoxy, cyano, trifluoromethyl, hydroxyalkyl, free, esterified, acidified or salified carboxy, amino, mono- or dialkylamino, the nitrogen atom of the pyridyl radical being optionally oxidized, $R_4$ and $R_5$ either are identical or different and represent an alkyl radical, optionally substituted by one or more radicals chosen from optionally esterified, etherified or protected hydroxyl radicals, halogen atoms and alkylthio and phenylthio radicals themselves optionally substituted by one or more radicals chosen from halogen atoms and the hydroxyl radical, or together form the:

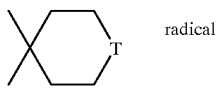

radical in which T represents an oxygen or sulphur atom, X and Y, identical or different, represent an oxygen or sulphur atom.

A more particular subject of the present invention is the preparation process as defined above for the products of formula (I) as defined above in which:
$R_1$ and $R_2$, identical or different, are such that one represents a hydrogen atom or a cyano radical and the other is chosen from halogen atoms and cyano and amino radicals, $R_3$ represents a hydrogen atom or an alkyl radical optionally substituted by an optionally esterified, etherified or protected hydroxyl radical,
$R_4$ and $R_5$, identical or different, represent a linear or branched alkyl radical containing at most 6 carbon atoms, optionally substituted by one or more radicals chosen from optionally esterified, etherified or protected hydroxyl radicals and halogen atoms and X and Y represent an oxygen atom.

An even more particular subject of the present invention is the preparation process as defined above for the following products
3-[4-amino-3-(trifluoromethyl) phenyl] 5,5-dimethyl 2,4-imidazolidine dione,
5,5-dimethyl-3-(4-iodo-3-(trifluoromethyl) phenyl) 2,4-imidazolidinedione,
4-(4,4-dimethyl-2,5-dioxo-1-imidazolidinyl)-2-(trifluoromethyl) benzonitrile,
4-(4,4-dimethyl-2,5-dioxo-3-(4-hydroxybutyl)-1-imidazolidinyl)-2-(trifluoromethyl)-benzonitrile,
4-(2,4-dioxo 1-(4-hydroxybutyl)-8-oxa-1,3-diazaspiro(4,5) decan-3-yl)-2-(trifluoromethyl) benzonitrile,
5,5-dimethyl-3-(4,5-dicyano-3-(trifluoromethyl) phenyl)-2,4-imidazolidinedione,
these products being in all possible racemic, enantiomeric or diastereoisomeric isomer forms, as well as their addition salts with the pharmaceutically acceptable mineral and organic acids or mineral and organic bases.

To implement the process indicated above, the operation is preferably carried out under the conditions indicated hereafter.

To obtain the product of formula ($A_1$), the operation is preferably carried out by using one half-moll of the compound of formula (III) per moll of the compound of formula (II), in dimethylformamide or preferably dimethylacetamide, at a temperature of approximately 0° C.

In a preferred manner, the compound of formula (III) is dimethyldibromohydantoin used in solution in dimethylacetamide and introduced into the orthotrifluorometylanilane of formula (II) itself in solution in dimethylacetamide while maintaining the temperature at approximately 0° C.

The compound of formula ($A_2$) which forms intermediately in situ, and which is not isolated, thus has a selective bromination which is situated in para position of the amino radical.

Then, in situ, a half-mol of compound B, i.e. dimethylhydantoin, is added, preferably in the presence of cuprous oxide at a temperature of approximately 155° C. and in this way the product formula ($A_1$) is obtained with a remarkable yield.

To isolate the product of formula ($A_2$), the reaction of the compound of formula (II) with the compound of formula (III) can be carried out in dimethylacetamide, preferably at a temperature of 0° C.

The compound of formula ($A_2$) can also be obtained by selective bromination by N-bromosuccinimide in solid form or in solution, choosing dimechylformamide or dimethylacetamide as solvent, preferably using a solvent such as water, acetone or other polar solvents usually employed.

In an unexpected manner, a remarkable selectivity of the bromination position is in fact observed under these conditions.

Also the operation is preferably carried out under these conditions at a temperature of 0 to 20° C.

The product of formula ($A_2$) thus obtained can be subjected to a reaction with a derivative of hydantoin, i.e. the compound of formula (IV), in order to obtain the product of formula ($A_3$); the operation is carried out in a solvent such as the triglyme, dimethylsulphoxide, diphenyl oxide, dimethylformamide or also and preferably dimethylacetamide.

The operation is preferably carried out in the presence of a catalyst such as copper in the native state or in the form of cuprous or cupric oxide.

The operation is preferably carried out in dimethylacetamide in the presence of cuprous oxide at a temperature of the order 165° C.

The product of formula (A) can then be subjected to a diazotation reaction such as for example by formation of the hydrochloride: in this way the diazonium salt (N=N$^\oplus$-, Cl$^\ominus$) is generated by reacting sodium nitrite in hydrochloric acid.

The diazonium salt thus obtained can be isolated if desired, in the form of the tetrafluoroborate (BF$_4^\ominus$) salt which is insoluble in water by treatment with sodium tetrafluoroborate (NaBF$_4$).

The diazonium salt i.e. the product of formula (V) obtained can then be subjected to a halogenation reaction in order to obtain the product of formula ($F_1$).

This halogenation can be a bromination by reaction, for example, of sodium or lithium bromide in a solvent such as for example a water/methylene chloride mixture or also, and preferably, an iodination by the action of sodium iodide in a water/methylene chloride mixture.

The product of formula ($F_1$) in which the halogen atom is a fluorine can also be obtained by heating the diazonium salt isolated above in the form of tetrafluoroborate at a temperature of the order of 60 to 80° C.

The product of formula ($F_1$) thus obtained can then be subjected to a substitution reaction on the halogen atom, which is preferably an iodine atom, to introduce the $R'_1$ radical and in this way to obtain the product of formula $F_2$. The operation is carried out in a solvent such as for example dimethylformamide. In the compounds of formulae (VI) and (VII), M represents a metal such as copper or nickel, or also palladium in particular to introduce an acetylenic. The compounds of formulae (VI) and (VII) can therefore in particular be copper cyanide or also trifluoro-methyl cuprate (CF$_3$Cu) obtained by the reaction of trimethyl-(trifluoromethyl) silane with potassium fluoride and copper iodide in dimethylformamide.

The halogenation reaction of the product of formula (A) to produce the product of formula ($F_3$) can be carried out under the usual conditions such as for example by bromination by N-bromo succinimide, in a solvent such as for example dimethylformamide at a temperature of the order of 20 to 30° C.: the halogen atom is thus introduced into the ortho position of the amino radical.

The product of formula ($F_3$) to produce the product of formula ($F_4$) can be subjected to a substitution reaction of the halogen atom by the $R'_2$ radical according to the usual conditions known to a man skilled in the art and in particular as defined above, to introduce the $R'_1$ radical onto the product of formula ($F_1$).

The amine of formula (F₄) thus obtained can be converted into the diazonium salt then halogenated and finally substituted on the halogen atom by the radical R'₁ under the same conditions as those described above, to thus produce the product of formula (F₅).

The halogenation reaction of the product of formula (F₃) into the product of formula (F₆) can be carried out according to the usual conditions in particular by formation of the diazonium salt on the amino radical then halogenation under the conditions defined above.

The product of formula (F₆) can in turn be substituted on the two halogen atoms in particular by the same cyano radical for example by the action of copper cyanide in dimethylformamide.

The products of formula (F₁), (F₂), (F₃), (F₄), (F₅) or (F₆) can be subjected to the action of the product of formula (IV) to produce the corresponding product of formula (I) under the conditions defined above for the reaction of the product of formula (A₂) with the product of formula (IV) to produce the product of formula (I').

The products of formulae (A₁), (A₃) and (I') thus obtained can then if necessary and if desired, be subjected to a substitution reaction by a halogenated derivative of formula R'₃-Hal in which R'₃ can in particular represent an acylated derivative such as in particular the ZO-alk-Hal compound in which alk represents an alkyl radical, Z an acyl radical such as in particular the acetyl radical or also a silyl radical and Hal represents a halogen atom such as preferably a bromine, iodine or chlorine atom, preferably fluorine.

The operation is carried out in a solvent such as for example and in particular dimethylformamide or dimethylacetamide in the presence of a strong base such as soda, sodium or potassium hydride. The operation can be carried out by phase transfer reaction in the presence of quaternary ammonium salts such as tert-butyl ammonium.

In this way the products of formula (I) are in particular obtained in which R₃ represents an alkyl radical substituted by a free, esterified, etherified or protected hydroxyl radical such as an acylated or silylated radical.

The optional reactive functions which can be carried by or represented by R|₁, R"₂, R'₃, R'₄ or R'₅ and which are optionally protected, can be in particular the hydroxy or amino functions. The usual protective groups are used to protected these functions. For example the following protective groups of the amino radical can be mentioned: tert-butyl, tert-amyl, trichloroacetyl, chloroacetyl, benzhydryl, trityl, formyl, benzyloxycarbonyl.

As a protective group of the hydroxy radical the radicals such as formyl, chloroacetyl, tetrahydropyrannyl, trimethylsilyl, tert-butyl dimethylsilyl can be mentioned.

Of course the above list is not limitative and other protective groups, for example known in the chemistry of the peptides, can be used. A list of such protective groups is found for example in the French Patent BF 2,499,995 the content of which is incorporated here by reference.

The optional elimination reactions of the protective groups are carried out as indicated in said Patent BF 2,499,995. The preferred method of elimination is acid hydrolysis using acids chosen from the following acids: hydrochloric, benzene sulphonic or paratoluene sulphonic, formic or trifluoroacetic. Hydrochloric acid is preferred. The optional esterification of products, in which R'₃ contains a free OH radical is carried out under standard conditions. For example an acid or a functional derivative can be used, for example an anhydride such as acetic anhydride in the presence of a base such as pyridine.

The optional esterification or salification of the products in which R'₃ contains a COOH group is carried out under standard conditions known to a man skilled in the art. - The optional amidification of products, in which R'₃ contains a COOH radical is carried out under standard conditions. A primary or secondary amine can be used on a functional derivative of the acid for example a symmetrical or mixed anhydride.

The conversion reaction of the >C=O group or groups into a >C=S group is carried out using a so-called Lawesson reagent of formula:

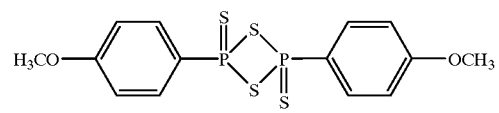

which is a product commercially available for example from the firm FLUKA and the use of which is described for example in the publication: Bull. Soc. Chim. Belg. Vol. 87, No. 3, (1987) p. 229.

When it is desired to convert two >C=O functions into two >C=S functions the operation is carried out in the presence of an excess of Lawesson reagent. The same is true when one starts from a molecule containing a >C=S function and a >C=O function and it is desired to convert said >C=O function into a >C=S function.

On the other hand when one starts from a molecule containing two >C=O functions and it is desired to obtain a product containing only a single >C=S function. The operation is carried out in the presence a deficit of Lawesson reagent. Then in general a mixture of three products is obtained: each of the two products containing a >C=O function and a >C=S function and the product containing two >C=S functions. These products can then be separated by the usual methods such as chromatography.

The conversion reaction of the amino radical into a nitro radical can be carried out under the usual conditions known to a man skilled in the art, such as in particular those described in the following references:

Emmons W. D., J. Am. Chem. Soc. 1957, 79, 5528,

Holmes R R and Bayer R p, J. Am. Chem. Soc. 1960, 82, 3454.

A preparation process for certain products of formula (I) as defined above is described in the French Patent No. 2,693,461.

A quite particular subject of the present invention is a preparation process for the products of formula (I) as defined above, characterized in that to obtain the product of formula (A₁) from the products of formulae (II), (III) and B, as defined above, the operation is carried out in a solvent chosen from dimethylsulphoxide, triglyme, dimethylacetamide or dimethylformamide and preferably dimethylacetamide.

A more particular subject of the present invention is a preparation process for the products of formula (I) as defined above, characterized in that the compound of formula (III) is the dibrominated derivative of formula:

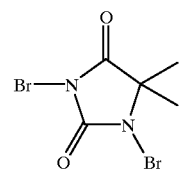

and that a half-mol of this compound and a half-mol of the compound of formula (3) are used per mol of the compound of formula (II).

An even more particular subject of the present invention is a preparation process for the products of formula (I) as defined above, characterized in that the reaction is carried out at a temperature of 130° C. to 160° C. and preferably at 155° C.

The starting products of formulae (II), (III), (B), (IV), (VI) and (VII) on which the process, which is a subject of the invention, is carried out in order to obtain the products of formula (I), are known and commercially available or can be prepared according to methods known to a man skilled in the art.

The products of formula (IV) which are derivatives of hydantoin are widely used and mentioned in the literature such as for example in the following articles:

J. Pharm. Pharmacol., 67, Vol. 19 (4), p. 209–16 (1967)
J. Chem. Soc., 74, (2), p. 219–21 (1972)
Khim. Farm. Zh., 67, Vol. 1 (5) p. 51–2
German Patent 2,217,914
European Patent 0,091,596
J. Chem. Soc. Perkin. Trans. 1, 74 (2) p. 48, p. 219–21.

A subject of the present invention is also as new industrial products, the following products:

3-[4-amino 3-(trifluoromethyl) phenyl]-5,5-dimethyl 2,4-imidazolidine dione,
5,5-dimethyl 3-(4-iodo 3-(trifluoromethyl) phenyl)-2,4-imidazolidinedione,
5,5-dimethyl 3-(4,5-dicyano 3-(trifluoromethyl) phenyl) 2,4- imidazolidinedione.

The examples given hereafter illustrate the invention without however limiting it.

EXAMPLE 1

3-[4-amino 3-(trifluoromethyl) phenyl]5,5-dimethyl 2,4-imidazolidine dione 100 g of O-trifluoromethylaniline is introduced at 20°±2° C. then 100 ml of dimethylacetamide is added while maintaining the same temperature. After cooling down under agitation at 0° C.±2° C. a solution of 88.8 g of dibromodimethylhydantoin and 100 ml of dimethylacetamide is then added over about 30 minutes while maintaining the temperature at 0° C.±2° C. The reaction medium is maintained under agitation for 30 minutes, then taken to 20° C.±2° C. and 40 g of dimethylhydantoin then 50 g copper oxide are added. The whole is heated under reflux for approximately 18 hours then cooled down to 20° C.±2° C., agitation is carried out for 30 minutes followed by filtering, separating and washing with 4×25 ml of dimethylacetamide. The resultant product is then poured into 300 ml of pure 22°Bé ammonium hydroxide and 300 ml of demineralized water under agitation over 1 hour at 20° C.±2° C., agitation is continued for 1 hour at 20° C.±2° C. then the whole is cooled down to 0° C.±5° C. and is maintained under agitation for another hour, followed by separating, washing at 20° C.±2° C., with 100 ml of pure 22°Bé ammonium hydroxide then with 4×100 ml of demineralized water and drying. In this way 155.8 g of expected product is obtained.

| Analyses: IR CHCl₃ (cm⁻¹) | | |
|---|---|---|
| NH/NH₂ | =C—NH₂ | 3510 |
| | =C—NH | 3449 |
| | =C—NH₂ | 3429 |

| -continued | |
|---|---|
| Analyses: IR CHCl₃ (cm⁻¹) | |
| >=O | 1781-1719 |
| Aromatics + NH₂ def. | 1637-1585-1516-1511 |

EXAMPLE 2

5,5-dimethyl-3-(4-iodo 3-(trifluoromethyl) phenyl) -2,4-imidazolidine dione 140 g of the product of Example 1 and 210 ml of demineralized water are introduced at 20°±2° C., agitation is carried out and 210 ml of pure 22°Bé hydrochloric acid is added over about 5 minutes. The reaction medium is maintained at 35°–40° C. for 30 minutes under agitation then cooled down to 0°±5° C. under agitation. Then 28 ml of methylene chloride is added, a solution of 43.7 g of sodium nitrite in 70 ml of demineralized water is then added over about 30 minutes, at 0°±5° C. The reaction medium is maintained for another hour under agitation at 0°±5° C., a solution of 87.7 g of sodium iodide in 140 ml of demineralized water is added over 45 minutes. The reaction medium is maintained under agitation for another hour and 700 ml of methylene chloride is added. Agitation is carried out for 15 minutes at 0°±5° C., 28 g of sodium metabisulphite is added in one go and agitation is carried out for another 30 minutes while leaving the temperature to return to 20° C. After pouring, the organic phase is decanted, the aqueous phase is reextracted with 280 ml of methylene chloride, then the organic phases are washed with 3×140 ml of a saturated aqueous solution of NaCl. The joint chloromethylenic phases are dried, followed by filtering and washing with 3×70 ml of methylene chloride and 184.5 g of expected product (white crystals) is obtained, M.p.=164–165° C.

EXAMPLE 3

4-(4,4-dimethyl-2,5-dioxo-1-imidazolidinyl)-2-(trifluoromethyl)-benzonitrile 184 g of the product of Example 2 is introduced at 20°±2° C. and 66.15 g of copper cyanide and 420 ml of dimethylformamide are added under agitation the whole is heated while distilling the methylene chloride until a temperature of 130° C. is obtained in the reaction medium and then it is maintained for 5 hours under agitation at this temperature. The medium is cooled down to 20°±2° C. under agitation, maintained for 1 hour under these conditions followed by separation and washing with 3×0.3 vol of dimethylformamide. Then 700 ml of pure 22°Bé ammonium hydroxide and 700 ml of demineralized water are added to the mixture agitated at 20°±2° C. Agitation is carried out for 1 hour at 20°±2° C. then the whole is cooled down to 0°±5° C., maintained for 1 hour under agitation at 0°±5° C., followed by separating and washing with 2×140 ml of pure 22°Bé ammonium hydroxide at 20°±2° C. then with 4×140 ml of demineralized water then drying. Purification is carried out by adding 1105 ml of ethyl acetate then taking to reflux under agitation and then 12.3 g of acticarbon black CX is added. The reaction medium is maintained under agitation under reflux for 30 minutes, then filtered, followed by washing with 3×61 ml of boiling ethyl acetate, concentration under agitation, cooling down under agitation to 0°±2° C. and maintaining under these conditions for 2 hours. Separation, washing with 3×37 ml of ethyl acetate at 0°±2° C. and drying are carried out. In this way 103.7 g of expected product (clear beige powder) is obtained.

M.p.° = 210° C.
Analyses: IR nujol (cm$^{-1}$)

| OH/NH region | max | 3340 |
|---|---|---|
| —C≡N | | 2245 |
| >=O | | 1789-1720 |
| Aromatics | | 1612-1575-1505 |

EXAMPLE 4

4-(4,4-dimethyl-2,5-dioxo-3-(4-hydroxybutyl) 1-imidazolidinyl)-2-(trifluoromethyl)-benzonitrile 300 ml of dimethylformamide and 100 g of the product of Example 3 are introduced at 20°/22° C. and the reaction medium is maintained under agitation at this temperature for approximately 5 minutes then 98.5 g of 4-bromobutyl acetate then 20 g of soda are added and the whole is maintained under agitation and under a nitrogen atmosphere at +20°/+22° C. for approximately 22 hours. While maintaining agitation, at this temperature, 20 g of soda is added then over approximately 5 minutes 400 ml of methanol is added and the whole is maintained in this way for 1 hour. While leaving the temperature to rise, 500 ml of demineralized water at +20° C. is introduced under agitation, then the reaction medium is placed under agitation, 500 ml of demineralized water is added at +20° C. and the whole is maintained under agitation for 1 hour at 25°/30° C., then cooled down under agitation to +0°/+5° C., and maintained for 2 hours, followed by separating, washing with 4×100 ml of demineralized water and drying. Purification is carried out by adding 696 ml of methylene chloride at 20°/22° C. and washing with 3×232 ml of demineralized water then drying, 5.8 g of supra black is added, the medium is maintained under agitation at 20°±2° C. for 2 hours followed by filtering and rinsing with 2×116 ml of methylene chloride. After concentrating under agitation, 116 ml of denat. ethanol toluene is added at 20° C. then 174 ml of demineralized water is added. The reaction medium is cooled down under agitation to 20°/22° C., maintained under agiatation for 2 hours at this temperature then cooled down to 0°±2° C. and maintained for 1 hour under these conditions, followed by separating, washing with 2×58 ml of ethanol with 50% water at 0°/+2° C. and drying. In this way 111.5 g of expected product (white powder) is obtained. M.p.=102° C.

EXAMPLE 5

4-(4,4-dimethyl 2,5-dioxo 1-imidazolidinyl) 2-(trifluoromethyl) benzonitrile

Stage 1: para-bromo ortho-trifluoromethyl aniline
1st method:
100 g of ortho trifluoromethylaniline and 200 ml of dimethylacetamide are introduced and the reaction medium is cooled down to 0°±2° C. 88.8 g of dibromo-dimethyl hydantoin is added over 30 minutes at 0°±2° C., the temperature is maintained at 0°±2° C. and agitation is carried out at 0°±2° C . for 15 minutes. Then the temperature is allowed to rise to 20° C. and the whole is poured into 200 ml of demineralized water at 20°±2° C. Agitation is carried out for 15 minutes, 400 ml of isopropyl ether is added, the aqueous phase is decanted and the organic phase is washed with 2×100 ml of demineralized water, the aqueous phases are reextracted with 100 ml of isopropyl ether and the combined organic phases are dried, filtered and washed with 2×20 ml of isopropyl ether. Concentration is carried out a temperature of 30–40° C. and in this way 149 g of expected product (orangy-brown oil) is obtained.
2nd method:
100 g of ortho trifluoromethylaniline and 200 ml of dimethylacetamide are introduced and 107.3 g of N-bromo succinimide in powder form is added over about 30 minutes at 20°±2° C. The temperature is maintained at 20°±2° C. and agitation is carried out under a nitrogen atmosphere at 20°±2° C. for 15 minutes, then the whole is poured into 200 ml of demineralized water at 20°±2° C., agitation is carried out for 15 minutes and 400 ml of isopropyl ether is added. The aqueous phase is decanted, the organic phase is washed with 2×100 ml of demineralized water, the aqueous phases are reextracted with 100 ml of isopropyl ether and the combined organic phases are dried, followed by filtering, washing with 2×20 ml of isopropyl ether, concentrating and in this way 149 g of expected product is obtained.
Analyses: IR on CHCl$_3$ (cm$^{-1}$)
=C—NH$_2$ 3520–3430
NH$_2$ def.+aromatics 1634–1610–1581–1492
Stage 2: p-bromo o-trifluoromethyl diazonium fluoroborate
120 g of the product obtained in Stage 1 above and 240 ml of demineralized water are introduced at 20° C., then 375 ml of 22°Bé concentrated hydrochloric acid is introduced over about 15 minutes, while leaving the temperature to rise to 35–40° C. Agitation is carried out for 30 minutes while leaving the temperature to drop to 20° C., followed by cooling down to 0° C.±2° C., and a solution of 240 ml of demineralized water and 72.5 g of sodium nitrite is introduced over about 30 minutes, while maintaining the temperature at 0° C.±2° C., followed by agitation for 1 hour while maintaining the temperature at 0° C.±2° C. 140 g of sodium tecrafluoroborate is added at this temperature and agitation is carried out while maintaining the temperature at 0° C.±2° C. for 1 hour, followed by filtering, rinsing with 2×50 ml of ice-cooled demineralized water and in this way 194.14 g of expected product is obtained.
Stage 3: p-bromo o-trifluoromethyl benzonitrile
13.5 g of copper cyanide and 400 ml of demineralized water are introduced at 20° C., the temperature is maintained at +20° C.±2° C., a solution of 41.6 g of sodium cyanide and 100 ml of demineralized water is added over 5 minutes, followed by cooling down to 0° C.±2° C. and 194 g of the diazonium salt obtained in Stage 2 above is introduced while maintaining this temperature over about 10 minutes. The reaction medium is maintained under agitation at 0° C.±2° C. for 1 hour then the temperature is allowed to rise to 20° C. and 50 ml of concentrated ammonium hydroxide and 1 liter of methylene chloride are added, followed by decanting, washing, drying, concentrating, taking up in 160 ml of heptane, filtering, drying and purifying by chromatographing on silica eluting with heptane-ethyl acetate (9-1) and in this way 86 g of expected product (white crystals) is obtained.
M.p.=30° C.

Analyses: IR CHCl₃ (cm⁻¹)
—C≡≡N ~2240
Aromatics 1598–1570–1488

Stage 4: 4-(4,4-dimethyl-2,5-dioxo-1-imidazolidinyl)-2-(trifluoromethyl)-benzonitrile 110 g of the product obtained in Stage 3 above and 275 ml of dimethyl acetamide are introduced at 200C. 31.7 g of copper oxide Cu₂O and 67.7 g of dimethyl hydantoin are added at 20° C. under agitation. The reaction medium is heated for about 5 hours at 165° C., left to cool down to 20° C., then filtered and rinsed with 3×55 ml of dimethyl acetamide. A solution of 550 ml of 22°Bé concentrated ammonium hydroxide and 550 ml of ice-cooled water is prepared and it is introduced over about 15 minutes at 0° C. and the reaction medium is left for about 1 hour at 0° C., followed by separating, washing with 110 ml of a 50% aqueous solution of ammonium hydroxide then with 4×110 ml of demineralized water. After drying, purification is carried out by adding 125 ml of toluene and 125 ml of acetonitrile then heating to 80° C. for 1 hour and leaving to cool down. Agitation is then carried out for 1 hour at 0° C., followed by filtering, separating and washing with 2×25 ml of an ice-cooled solution (acetonitrile/toluene (1:1)). After drying, 104.4 g of expected product is obtained in this way. M.p.=210° C.

EXAMPLE 6

4-(4,4-dinethyl-2,5-dioxo-1-imidazolidinyl)-2-(trifluoromethyl)-benzonitrile Stage 1: 3-(trifluoromethyl)-4-cyano chloro benzene 100 g of 2-trifluoromethyl-4-chloro iodobenzene, 200 ml of dimethylformamide and 58.7 g of copper cyanide are introduced at 20° C., the reaction medium is heated for 3 hours at 140° C., left to cool down to 20° C., then poured into 600 ml of ice-cooled demineralized water. After filtering, rinsing with 3×200 ml of isopropyl ether, the aqueous phase is decanted and reextracted with 3×200 ml of isopropyl ether. The organic phases are combined and washed with 200 ml of demineralized water and dried. In this way 66.64 g of expected product is obtained.
Analyses: IR on CHCl₃ (cm⁻¹)
C=N ~2238
Aromatics 1601–1570

Stage 2: 4-(4,4-dimethyl-2,5-dioxo-1-imidazolidinyl)-2-(trifluoromethyl)-benzonitrile 4.47 g of the product obtained in Stage 1 above, 11.2 ml of triglyme, 2.78 g of 5,5-dimethyl hydantoin and 1.34 g of cuprous oxide are introduced then the suspension is agitated and taken to 215° C. for 4 hours. Then it is returned to ambient temperature, followed by filtering, washing with 4.5 ml of triglyme and agitating without exceeding 25° C., 4.5 ml of 22°Bé concentrated ammonium hydroxide, 26 ml of water and 4.5 ml of toluene. Agitation is carried out for 15 minutes at 20° C. then the reaction medium is cooled down to −10° C., agitation is carried out for 1 hour, followed by separating, washing with 2.2 ml of toluene then 4.5 ml of water and drying. In this way 1.98 g of expected product (brown crystals) is obtained. M.p.=210° C.

| Analyses: IR nujol (cm⁻¹) | |
|---|---|
| OH/NH absorption | ~3340 |
| C≡N | ~2240 |
|  | 1788-1721 |
| Aromatics | 1610-1572-1504 |

EXAMPLE 7

5,5-dimethyl-3-(4,5-dicyano-3-(trifluoromethyl) phenyl) 2,4-imidazolidinedione Stage 1: 3-(5,5-dimethyl-2,4-imidazolidine)-2-amino 3-(trifluoromethyl) bromo benzene 20 g of the product of Example 1 and 40 ml of dimethylacetamide are introduced at 20±2° C., followed by cooling down to +10° C.±2° C. and 12.5 g of N-bromo succinimide in powder form is added over about 30 minutes at 10° C.±2° C. and under agitation and under a nitrogen atmosphere. The temperature is maintained at 10° C.±2° C., agitation is carried out for 15 minutes, the temperature is allowed to rise to 20° C. then agitation is carried out for 1 hour. The reaction medium is poured into 200 ml of methylene chloride, 100 ml of 30 demineralized water is introduced at 20° C.±2° C., followed by decanting, washing the organic phase with 2×50 ml of demineralized water at 20° C.±2° C., drying and concentrating. In this way 22 g of expected product is obtained.

Stage 2: 4-(5,5-dimethyl-2,4-imidazolidinedione)-2-bromo 5-(trifluoromethyl) iodo benzene 20 g of the product obtained in Stage 1 above and 30 ml of demineralized water are introduced at 20° C. and 30 ml of 22Bé concentrated hydrochloric acid is introduced over 15 minutes, while allowing the temperature to rise to 35–40° C. Agitation is carried out for 30 minutes while allowing the temperature to drop to 20° C., followed by cooling down to 0° C.±2° C. and a solution of 12 ml of demineralized water and 4.9 g of sodium nitrite is introduced over 30 minutes while maintaining this temperature. Agitation is carried out for 1 hour while maintaining this temperature and under agitation 100 ml of methylene chloride is added then a solution of 9.83 g of sodium iodide and 10 ml of demineralized water is added over 30 minutes and the reaction medium is maintained under agitation for 1 hour at 0° C.±2° C., then the temperature is allowed to rise to 10° C. Then 4 g of sodium metabisulphite is added, followed by decanting, the chloromethylenic phase is washed with water, dried and concentrated. In this way 18.5 g of expected product is obtained.

| Analyses: CHCl₃ (cm⁻¹) | |
|---|---|
| =C—NH | 3446 |
|  | 1790-1730 |

-continued

| Analyses: CHCl$_3$ (cm$^{-1}$) | |
|---|---|
| Aromatics | 1597-1560 |

Stage 3: 5,5-dimethyl-3-(4,5-dicyano 3-(trifluoromethyl) phenyl)-2,4-imidazolidinedione 13 g of the product obtained in Stage 2 above, 26 ml of dimethylformamide, 2.7 g of copper cyanide and 1.47 g of sodium cyanide are introduced at 20° C. and the reaction medium is heated for 20 hours at 150° C. Then it is left to cool down to 20° C., poured into a mixture of 50 ml of demineralized water and 50 ml of 22° pure ammonium hydroxide, followed by filtering, rinsing with 3×50 ml of methylene chloride, the aqueous phase is decanted and reextracted with 3×50 ml of methylene chloride. The organic phases are combined and washed with 50 ml of demineralized water and dried. The chloromethylenic phase is agitated for one hour at 20° C. with 1.5 g of acticarbon black and the methylene chloride is evaporated off and replaced with 30 ml of isopropyl ether. Separation is carried out at 20° C., followed by washing with 3×10 ml of isopropyl ether and drying. Purification is carried out by chromatography on silica eluting with methylene chloride-ethyl acetate (95-5), then by dissolution in isopropanol under reflux, filtering, rinsing with isopropanol, concentrating, ice-cooling for 1 hour, separating and drying. In this way 3.1 g of expected product (white crystals) is obtained. M.p.=159–160° C.

| Analyses: IR | |
|---|---|
| OH/NH | 3403-3388 |
| C≡N | 2236 |
| =O | 1776-1738-1729 |
| Aromatics | 1606-1575-1502. |

EXAMPLE 8

4-(2,4-dioxo 8-oxa 1,3-diaza spiro[4,5]decan 3-yl) 2-trifluoromethyl) aminobenzyl A mixture of 7 g of para-bromo-orthotrifluoromethyl-aniline obtained in Stage 1 of Example 5, 15 ml of dimethylacetamide, 2.33 g of cuprous oxide and 6 g of 5[spiro(4-pyran)] 2,4-imidazolidine dione (the preparation of which is given hereafter) is agitated for 18 hours at 150° –155° C. The reaction medium is cooled down to 20–22° C., filtered, washed with 2 times 7 ml of dimethylacetamide and poured into 200 ml of water. Agitation is carried out for 1 hour at ambient temperature, followed by separating and washing with a mixture of water and 20% ammonium hydroxide (50/50) then with water. After drying at 40° C., 9.1 g of the desired product is collected.

PREPARATION OF: 5[spiro(4-pyran)] 2,4-imidazolidine dione used at the start of Example 8.

5 g of tetrahydro-4h-pyran-4-one, 25 ml of demineralized water, 25 ml of ethanol, 7.2 g of potassium cyanide and 57 g of ammonium carbonate are heated for 4 hours at 45–50° C. Concentration under reduced pressure is carried out to dryness. The dry extract is taken up in 50 ml of water, separated, washed and dried at 40° C. 7.2 g of expected product is obtained.

NMR spectrum (DMSO)
1.47–1.84: the CH$_2$-C's; 3.59–3.81: the CH$_2$O's; 8.57–10.67: the NH-C=O's.

EXAMPLE 9

4-(2,4-dioxo 8-oxa 1,3-diaza spiro[4,5]decan 3-yl) 2-trifluoromethyl) iodobenzyl The operation is carried out as in Example 2, starting with 8 g of the product obtained in Example 8 using 10 ml of 22°Bé hydrochloric acid, 2.18 g of sodium nitrite and 5.5 g of sodium iodide. In this way 8.9 g of the desired product is collected.

EXAMPLE 10

4-(2,4-dioxo 8-oxa 1,3-diaza spiro[4,5]decan 3-yl) 2-trifluoromethyl) benzonitrile The operation is carried out as in Example 3, using 3.2 g of copper cyanide. After recrystallization from isopropanol, 1.8 g of the desired product is collected.
NMR spectrum: CDCl$_3$
1.78 (m), 2.55 (m): C—CH$_2$; 3.70 (m), 4.13 (m): CHO; 6.21 (s): CONH; 7.95 (m), 8.11 (m): aromatic H's.

EXAMPLE 11

4-(2,4-dioxo 1-(4-hydroxybutyl) 8-oxa 1,3-diaza spiro[4,5]decan 3-yl) 2-trifluoromethyl) benzonitrile 55 g of sodium hydride at 50% in oil is introduced and 340 mg of the product obtained in Example 10 in solution in 25 ml of dimethylformamide is added over 25 minutes, 20 minutes after the release of hydrogen has finished, 0.41 g of 4-iodobutoxy trimethylsilane is added and agitation is carried out for 18 hours at ambient temperature. The reaction medium is poured into 10 ml of water, followed by extraction with ethyl ether, washing with water then with salt water and drying, 10 ml of methanol and 1 ml of 2N hydrochloric acid are added, agitation is carried out 30 minutes and the whole is poured into 20 ml of water saturated with NaCl, extracted with chloroform, the extracts are dried, evaporated to dryness and the residue is chromatographed on silica eluting with a methylene chloride-acetone (8-2) mixture. 369 mg of the desired product is obtained.
I.R. Spectrum (CHCl$_3$) cm$^{-1}$
OH 3626–3485
C≡N 2235
C=O 1775–1721
aromatics 1615–1602–1575–1505.

What is claimed is:

1. A process for the preparation of all racemic, enantiomeric and diastereoisomeric forms of a compound of the formula

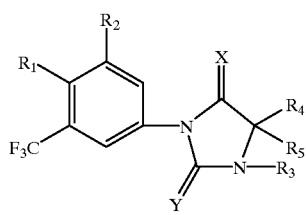

I wherein R$_1$ and R$_2$ are individually selected from the group consisting of hydrogen, halogen, alkyl, alkenyl and alkynyl of up to 6 carbon atoms, alkoxy, alkenyloxy and alkynyloxy of up to 6 carbon atoms, phenyl, phenoxy, —NO$_2$, —CF$_3$, —CN, —NH$_2$, acyl of an organic carboxylic acid of 1 to 6 carbon atoms, mono and dialkyl amino of 1 to 6 carbon atoms, salified carboxy, carboxy, carboxy esterified with alkanol of 1 to 6 carbon atoms and

R$_3$ is selected from the group consisting of hydrogen, alkyl, alkenyl and alkynyl of up to 6 carbon atoms unsubstituted or substituted and aryl and aryalkyl of up to 10 carbon atoms optionally substituted, the substituents being at least one member of the group consisting of hydroxy, halogen

alkoxy, alkenyloxy and alkynyloxy of up to 6 carbon atoms, uninterupted or interrupted by at least one member of the group consisting of —O—, —S—, —SO—, —SO$_2$— and —NH—, —CF$_3$, —SH, —CN, acyl and acyloxy of an organic carboxylic acid of 1 to 6 carbon atoms, carboxy, salified carboxy, carboxy esterified with alkyl of 1 to 6 carbon atoms,

—NH$_2$, —NH$_2$, mono- and dialkylamino of 1 to 6 carbon atoms, arylthio and cycloalkyl of 3 to 6 carbon atoms, aryl and cycloalkyl being unsubstituted or substituted with a member of the group consisting of alkyl, alkenyl and alkynyl of up to 6 carbon atoms, R$_4$ and R$_5$ are individually selected from the group consisting of hydrogen, alkyl of 1 to 6 carbon atoms unsubstituted or substituted with at least one member of the group consisting of halogen, —OH,

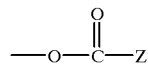

and alkoxy of 1 to 6 carbon atoms and phenylthio and alkylthio wherein the sulfur is unoxidized or oxidized to sulfone or sulfoxide and the latter may unsubstituted or substituted with at least one member of the group consisting of halogen, —OH, alkoxy of 1 to 6 carbon atoms,

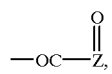

carboxy, salified carboxy, carboxy esterified with alkyl of 1 to 6 carbon atoms,

NH$_2$ and mono- and dialkylamino of 1 to 6 carbon atoms, Z is alkyl of 1 to 6 carbon atoms or R$_4$ and R$_5$ taken with the carbon atom to which they are attached form a 4 to 6 ring membered heterocyclic containing oxygen or sulfur and X and Y are individually —O— or —S— and their non-toxic, pharmaceutically acceptable addition salts with acids or bases comprising the preparation of a compound of the formula

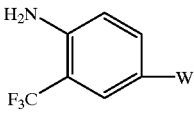

A wherein W is halogen or a hydantoin of the formula

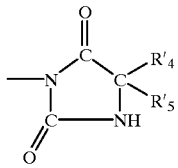

wherein R'$_4$ and R'$_5$ have the definition of R$_4$ and R$_5$ with reactive groups protected by reacting a compound of the formula

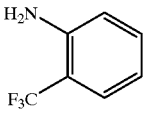

II either first with a compound of the formula

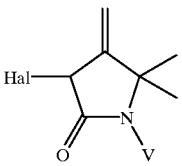

III wherein Hal is halogen and V is hydrogen or halogen and then with a compound of the formula

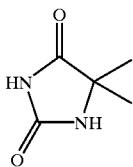

to obtain a compound of the formula

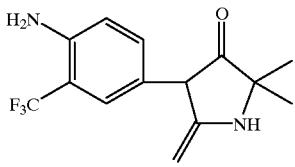

corresponding to a compound of Formula A wherein W is

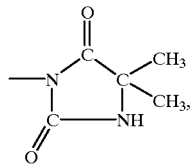

or with N-bromosuccimide in dimethylformamide or with a compound of Formula III to obtain a compound of the formula

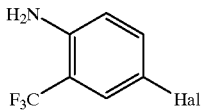

wherein Hal is halogen, reacting the latter with a compound of the formula

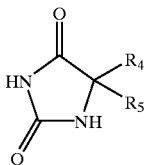

to obtain a compound of the formula

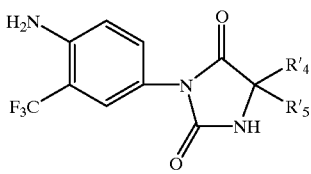

corresponding to the compound of Formula A wherein W is

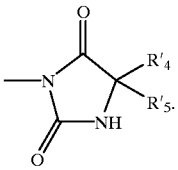

2. The process of claim 1 wherein $R_1$ and $R_2$ are individually selected from the croup consisting of hydrogen, halogen, —$CF_3$, —$NH_2$, mono- and dialkylamino of 1 to 6 carbon atoms and alkyl, alkenyl and alkynyl of up to 6 carbon atoms, $R_3$ is selected from the group consisting of hydrogen, alkyl uninterrupted or interrupted with at least one —O— or —S—, phenyl and pyridyl with the group other than hydrogen being unsubstituted or substituted with at least one member of the group consisting of halogen, phenyl, —OH, alkoxy of 1 to 6 carbon atoms,

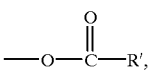

—CN, —$CF_3$, hydroxy alkyl of 1 to 6 carbon atoms, —$NH_2$, carboxy, salified carboxy, carboxy esterified with alkanol of 1 to 6 carbon atoms,

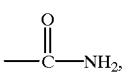

and mono-,
and dialkylamino of 1 to 6 carbon atoms with the nitrogen of pyridyl unoxidized or oxidized, R' is alkyl of 1 to 6 carbon atoms, $R_4$ and $R_5$ are individually alkyl of 1 to 6 carbon atoms unsubstituted or substituted by at least one member of the group consisting of —OH, alkoxy of 1 to 6 carbon atoms,

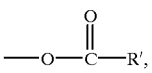

halogen, alkylthio of 1 to 6 carbon atoms and phenylthio, the latter two unsubstituted or substituted with halogen or —OH or $R_4$ and $R_5$ together form

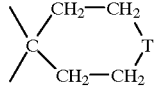

and X, Y and T are individually —O— or —S—.

3. The process of claim 1 wherein in the compound of Formula I, one of $R_1$ and $R_2$ is hydrogen or —CN and the other is hydrogen or —CN or —$NH_2$, $R_3$ is selected from the group consisting of hydrogen, alkyl of 1 to 6 carbon atoms unsubstituted or substituted with a member of the group consisting of alkoxy of 1 to 6 carbon atoms and

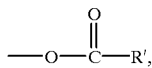

R' is alkyl of 1 to 6 carbon atoms, $R_4$ and $R_5$ are individually alkyl of 1 to 6 carbon atoms unsubstituted or substituted with at least one member of the group consisting of halogen, —OH, alkoxy of 1 to 6 carbon atoms,

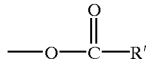

and X and Y are oxygen.

4. The process of claim 1 wherein the reaction with the compounds of Formulae II, III and B are effected in an organic solvent selected from the group consisting of dimethylsulfoxide, triglycine, dimethylacetamide and dimethylformamide.

5. The process of claim 4 wherein the organic solvent is dimethylacetamide.

6. The process of claim 1 wherein the compound of Formula III is

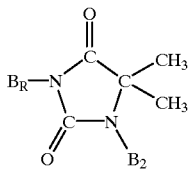

and one half mole of Formulae III and B are used per mole of the compound of Formula II.

7. The process of claim 6 wherein the compounds are reacted at 130° to 160° C.

8. The process of claim 6 wherein the compounds are reactive at about 155° C.

9. The process of claim 1 wherein the final product is selected from the group consisting of 3-[4-amino-3-(trifluoromethyl) phenyl] 5,5-dimethyl 2,4-imidazolidine dione, 5,5-dimethyl-3-(4-iodo-3-(trifluoromethyl) phenyl) 2,4-imidazolidinedione, 4-(4,4-dimethyl-2,5-dioxo-1-imidazolidinyl)-2-(trifluoromethyl) benzonitrile, 4-(4,4-dimethyl-2,5-dioxo-3-(4-hydroxybutyl)-1-imidazolidinyl)-2-(trifluoromethyl)-benzonitrile, 4-(2,4-dioxo 1-(4-hydroxybutyl)-8-oxa-1,3-diazaspiro(4,5) decan-3-yl)-2-(trifluoromethyl) benzonitrile, 5,5-dimethyl-3-(4,5-dicyano-3-(trifluoromethyl) phenyl)-2,4-imidazolidinedione, these products being in all possible racemic, enantiomeric or diastereoisomeric isomer forms, as well as their addition salts with pharmaceutically acceptable mineral and organic acids or mineral and organic bases.

* * * * *

UNITED STATES PATENT AND TRADEMARK OFFICE
CERTIFICATE OF CORRECTION

PATENT NO.    : 6,107,488
DATED         : August 22, 2000
INVENTOR(S)   : Bouchet et al.

It is certified that error appears in the above-identified patent and that said Letters Patent is hereby corrected as shown below:

<u>Column 23,</u>
Please replace the last formula 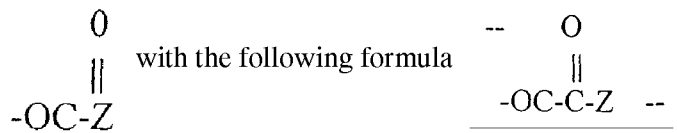 with the following formula <u>Column 24,</u>
Please replace the formual III 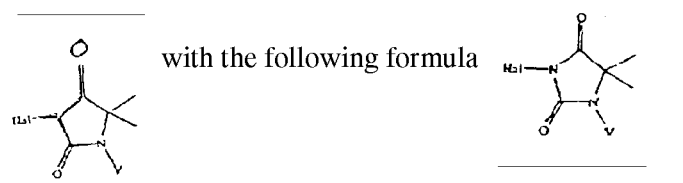 with the following formula <u>Column 25,</u>
Please replace the second formula 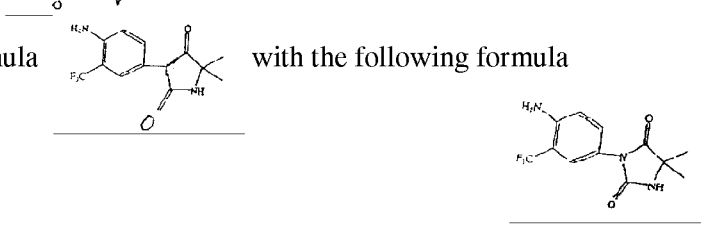 with the following formula Signed and Sealed this Thirtieth Day of March, 2004

JON W. DUDAS
*Acting Director of the United States Patent and Trademark Office*